US009545259B2

(12) United States Patent
Gavriely et al.

(10) Patent No.: US 9,545,259 B2
(45) Date of Patent: Jan. 17, 2017

(54) METHOD AND SYSTEM FOR OPTIMIZATION OF AN EXSANGUINATION TOURNIQUET

(71) Applicant: OHK MEDICAL DEVICES, LTD., Haifa (IL)

(72) Inventors: Noam Gavriely, Haifa (IL); Or Riven, Palyam (IL); Oded Fishelzon, Haifa (IL)

(73) Assignee: OHK MEDICAL DEVICES, LTD. (IL)

( * ) Notice: Subject to any disclaimer, the term of this patent is extended or adjusted under 35 U.S.C. 154(b) by 163 days.

(21) Appl. No.: 14/292,993

(22) Filed: Jun. 2, 2014

(65) Prior Publication Data

US 2015/0342614 A1   Dec. 3, 2015

(51) Int. Cl.
*A61B 17/132* (2006.01)

(52) U.S. Cl.
CPC ...... *A61B 17/1322* (2013.01); *Y10T 29/49828* (2015.01); *Y10T 29/49865* (2015.01)

(58) Field of Classification Search
CPC ............ A61B 17/1327; A61B 17/1325; A61B 17/132; A61F 2013/00468
See application file for complete search history.

(56) References Cited

U.S. PATENT DOCUMENTS

| | | | |
|---|---|---|---|
| 2,333,237 A | 11/1943 | Erekson | |
| 4,781,189 A | 11/1988 | Vijil-Rosales | |
| 5,181,522 A | 1/1993 | McEwen | |
| 5,607,448 A | 3/1997 | Stahl | |
| 5,916,183 A * | 6/1999 | Reid | 601/134 |
| 7,854,748 B2 | 12/2010 | Gavriely | |
| 2003/0040691 A1* | 2/2003 | Griesbach, III | A61F 13/0273 602/45 |
| 2004/0147956 A1 | 7/2004 | Hovanes et al. | |
| 2005/0080450 A1* | 4/2005 | Gavriely | 606/201 |
| 2005/0251181 A1* | 11/2005 | Bachmann | 606/157 |
| 2005/0261617 A1* | 11/2005 | Hall | A61F 13/08 602/62 |
| 2008/0125688 A1* | 5/2008 | Kellogg | A61F 13/00038 602/61 |
| 2009/0248061 A1 | 10/2009 | Gavriely et al. | |

FOREIGN PATENT DOCUMENTS

CN    2659349    12/2004

OTHER PUBLICATIONS

Gavriely et al.: "Method and System for Optimization of an Exsanguination Tourniquet", U.S. Appl. No. 14/292,980, filed Jun. 2, 2014.
International Search Report and Written Opinion PCT/IL2014/050499, dated Sep. 21, 2014.

* cited by examiner

*Primary Examiner* — Alexander Orkin
(74) *Attorney, Agent, or Firm* — Heslin Rothenberg Farley & Mesiti, P.C.; Jacquelyn A. Graff, Esq.

(57) ABSTRACT

The exsanguination tourniquet includes a constricting member and at least one sleeve removably coupled to the constricting member. The system includes the exsanguination tourniquet and an applicator device. The method of assembling includes obtaining a constricting member, obtaining at least one sleeve, and wrapping the at least one sleeve around the constricting member.

10 Claims, 11 Drawing Sheets

400

500

METHOD AND SYSTEM FOR OPTIMIZATION OF AN EXSANGUINATION TOURNIQUET

CROSS REFERENCE TO RELATED APPLICATIONS

The present application is related to U.S. patent application Ser. No. 14/282,980 entitled "METHOD AND SYSTEM FOR OPTIMIZATION OF AN EXSANGUINATION TOURNIQUET" and PCT Application No. PCT/IL2014/050499 entitled "METHOD AND SYSTEM FOR OPTIMIZATION OF AN EXSANGUINATION TOURNIQUET" filed on the date of filing of the present application, which are incorporated herein by reference in their entirety.

FIELD OF INVENTION

This invention relates to the field of healthcare of humans and non-human mammals, and more specifically to the modification of blood flow in a limb.

BACKGROUND

Creation of a blood free surgical field during orthopedic, vascular and plastic surgery has been the standard of care for over 100 years. The initial device was described by Friederich August von Esmarch in 1873 and is still being used today as the Esmarch bandage. In 1908, Dr. Harvey Cushing first described the use of a pneumatic tourniquet to occlude the blood flow into the scalp during brain surgery. Combination of an Esmarch bandage for squeezing the blood away from a limb (exsanguination) and a pneumatic tourniquet to occlude arterial blood flow is currently used in over 90% of limb operations. The use of a pneumatic tourniquet to occlude the arterial blood flow into a limb is associated with a number of side effects and adverse reactions. The side effects and adverse reactions may include tourniquet paralysis, which is transient or permanent nerve damage caused by the mechanical affect of the wide tourniquet cuff on the nerve. (Ochoa at el. Anatomical changes in peripheral nerves compressed by a pneumatic tourniquet. J Anat. 1972; 113(Pt 3):433-55.) In addition, side effects and adverse reactions may include skin lesions, which are skin abrasions or liquid blisters at the site of tourniquet placements (tourniquet burn) and tourniquet pain, which is tenderness at the site where the tourniquet was placed, that may last for days or even weeks.

More recently devices combining the exsanguination effect of the Esmarch and the blood flow blocking of a tourniquet are being used. This new class of devices is called exsanguination tourniquets. This new technology not only acts as a tourniquet, but is also capable of shifting blood from one part of the limb to another or to the central circulation. Exsanguination tourniquets are described in details in U.S. Pat. Nos. 4,848,324 and 7,854,748 which are included herewith as reference. An important aspect of an exsanguination tourniquet is the need to maintain the pressure applied to the limb in a safe range to avoid crush injuries to the tissues beneath it at any point along the limb. At the same time, it is also critical that the pressure applied by the exsanguination tourniquet is sufficient in order to block the arterial blood flow into the limb.

SUMMARY OF INVENTION

Shortcoming of the prior art are overcome and additional advantages are provided through the provision of a method for determining at least one parameter of at least one component used to construct a safe and effective exsanguination tourniquet. The method includes: obtaining, by a processor, at least one parameter related to a material comprising the exsanguination tourniquet; obtaining, by the processor, at least one parameter related to the positioning of the exsanguination tourniquet on a given limb; obtaining, by the processor, identifying information comprising a description of at least one component of the exsanguination tourniquet; based on the identifying information, selecting program instructions for execution by the processor, wherein the program instructions comprise a relationship between a compressive pressure of the at least one component of the exsanguination tourniquet, the at least one parameter related to the material comprising the exsanguination tourniquet, and the at least one parameter related to the positioning of the exsanguination tourniquet, wherein the program instructions are stored on a computer readable storage medium; determining, by the processor, a compressive pressure of the exsanguination tourniquet by executing the selected program instructions; and determining, by the processor, if the compressive pressure of the exsanguination tourniquet is optimized by comparing the compressive pressure to one or more predefined values, wherein the one or more predefined values are stored on a computer readable storage medium.

Computer systems, computer program products and methods relating to one or more aspects of the technique are also described and may be claimed herein. Further, services relating to one or more aspects of the technique are also described and may be claimed herein.

In another aspect, an exsanguination tourniquet is provided which includes, for instance: a constricting member and at least one sleeve removably coupled to the constricting member.

In yet another aspect, an exsanguination tourniquet system is provided which includes, for instance: a constricting member; at least one sleeve removably coupled to the constricting member; and an applicator device.

In a further aspect, a method of assembling an exsanguination tourniquet is provided which includes, for instance: obtaining a constricting member; obtaining at least one sleeve; and wrapping the at least one sleeve around the constricting member.

Additional features are realized through the techniques of the present invention. Other embodiments and aspects of the invention are described in detail herein and are considered part of the claimed invention. For example, embodiments of the present invention utilize one parameter related to a material comprising an exsanguination tourniquet that is obtained from a tensile test machine communicatively coupled to the processor via a network connection, one parameter related to a component that is an elastic ring, one parameter related to the positioning of the exsanguination tourniquet on the given limb relative to the end of an extremity on the limb, and verifying the compressive pressure of the exsanguination tourniquet.

BRIEF DESCRIPTION OF DRAWINGS

One or more aspects of the present invention are particularly pointed out and distinctly claimed as examples in the claims at the conclusion of the specification. The foregoing and objects, features, and advantages of one or more aspects of the invention are apparent from the following detailed description taken in conjunction with the accompanying drawings.

DETAILED DESCRIPTION OF THE INVENTION

The computer system, method, and computer program product disclosed herein address the challenge of determining one or more parameters and/or dimensions for an exsanguination tourniquet, that can be applied to a limb in a safe range to avoid crush injuries to the tissues beneath it at any point along the limb, but also apply pressure sufficient to block the arterial blood flow into the limb.

Specific challenges addressed by aspects of the present technique include, but are not limited to, determining parameters for an exsanguination tourniquet for foot and ankle applications, determining parameters for an exsanguination tourniquet for forearm applications, determining parameters for an exsanguination tourniquet for oversize thick leg applications, and determining parameters for an exsanguination tourniquet for grossly oversize thick leg applications.

In an aspect of the present technique, an embodiment of the present invention obtains properties of the materials used to construct an exsanguination tourniquet, and/or the physical dimensions of the exsanguination tourniquet, and/or the placement of the exsanguination tourniquet when in use to determine at least one parameter that can be utilized to design at least one exsanguination tourniquet, adapted for one or more specific applications.

In another aspect of the present technique, an embodiment of the present invention obtains properties of the materials used to construct an exsanguination tourniquet, and/or the physical dimensions of the exsanguination tourniquet, and/or the placement of the exsanguination tourniquet when in use to verify the efficacy of at least one exsanguination tourniquet, adapted for one or more specific applications.

In another aspect of the present invention, properties of the materials used to construct an exsanguination tourniquet, and/or the physical dimensions of the exsanguination tourniquet, and/or the placement of the exsanguination tourniquet when in use, are utilized to monitor the pressure of the tourniquet to maintain a uniform pressure profile across the site to which the exsanguination tourniquet is applied. As understood by one of skill in the art, a pressure profile is uniform when at any point the pressure is no more than 20% more or less than the average value of the pressure profile.

Figure 1:
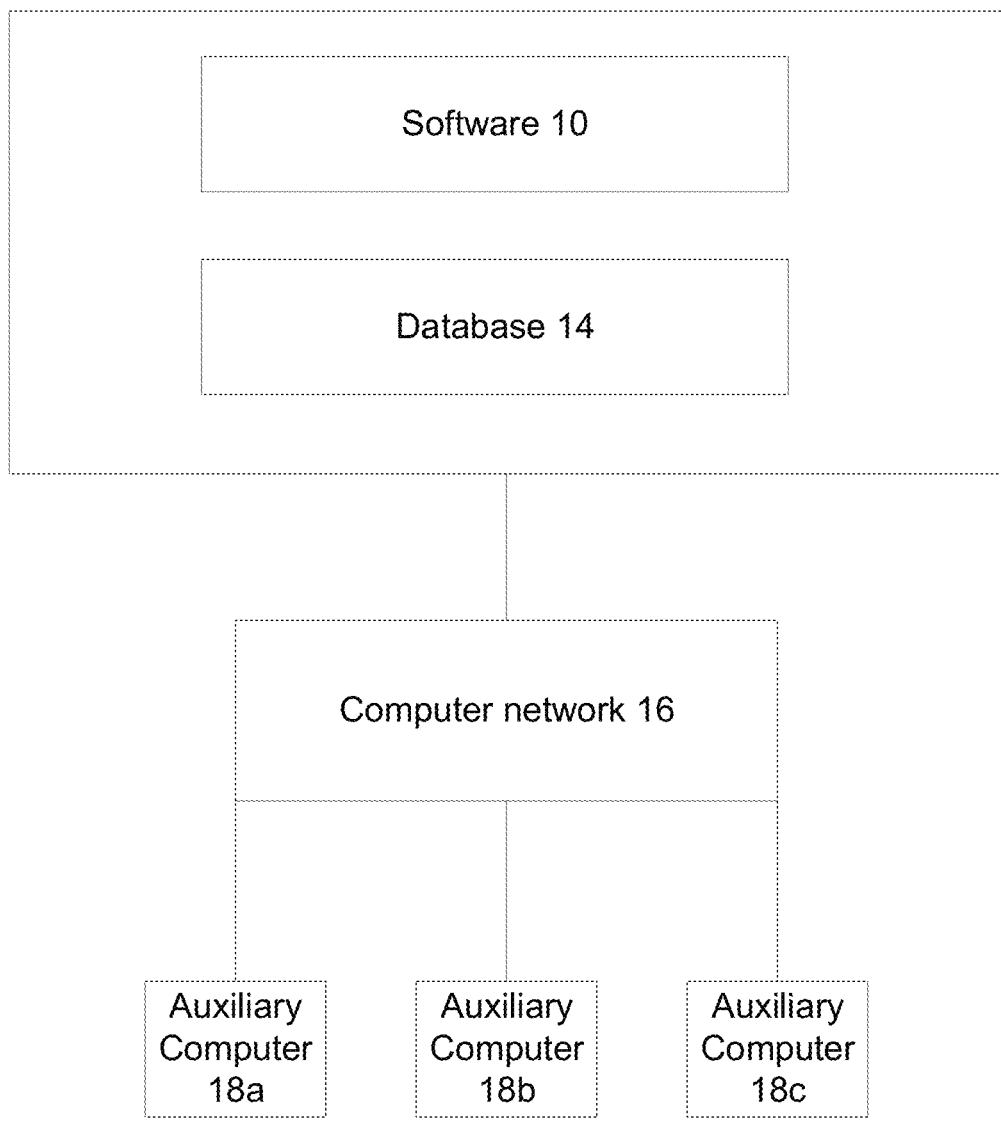
FIG. 1 depicts one example of an aspect a computing environment used to execute one or more aspects of an embodiment of the present invention.

FIG. 1 is a computer system 100 configured to perform at least one aspect of an embodiment of the present invention. In the embodiment of FIG. 1, software 10 is executed by at least one processor on a computer, termed a base computer 12 in FIG. 1 for clarity. The terms software, program code, computer program code, code, computer program product, and executable instructions, are used interchangeably throughout this application.

The software comprises code that is accessible to the processor and executable by at least one processor of the computer 12. The software can be stored on a memory on the physical computer 12, and/or in a memory and/or on removable media accessible to the computer 12 via a network connection, including but not limited to, a wireless and/or wireless network, utilizing a protocol known to one of skill in the art. The computer may also be configured to act as a web server, which may be capable of running the software and hosting and/or interacting with the database 14.

The base computer 12, as well as any other computer described in the present specification can include personal computers, servers, smart phones, mobile devices, laptops, desktops, and/or any means of personal or corporate computing device capable of executing the software 10 or portions of the software 10, or communicating with a computer executing the software 10 over a wireless or hard wired network.

In the embodiment of FIG. 1, the base computer is connected to a computer network 16, including but not limited to private and publicly accessible wired and wireless networks, and the Internet. In this embodiment, one or more computers, termed auxiliary computers 18a-18c are communicatively connected to the computer 12 via a computer network 16, including but not limited to, the Internet. The auxiliary computer 18a-18c receive data from the computer 12, via, for example, the web server on the computer 12 and the auxiliary computers 18a-18c can render (for viewing) determinations of parameters served by the base computer 12, and the base computer can obtain data from the auxiliary computers 18a-18c, including but not limited to, properties of the materials used to construct an exsanguination tourniquet, and the physical dimensions of the limb(s) to which an exsanguination tourniquet is to be applied.

The base computer 12 in the embodiment of FIG. 1 includes a database 14. Additional embodiments of the present invention utilize databases and other memory devices in different physical locations that are remotely accessible to the base computer 12 executing the software 10. In the embodiment of FIG. 1, the database 14 stores data regarding the properties of the materials used to construct an exsanguination tourniquet, as well as data related to various parameters affecting the utilization of embodiments of the technique.

Figure 2:
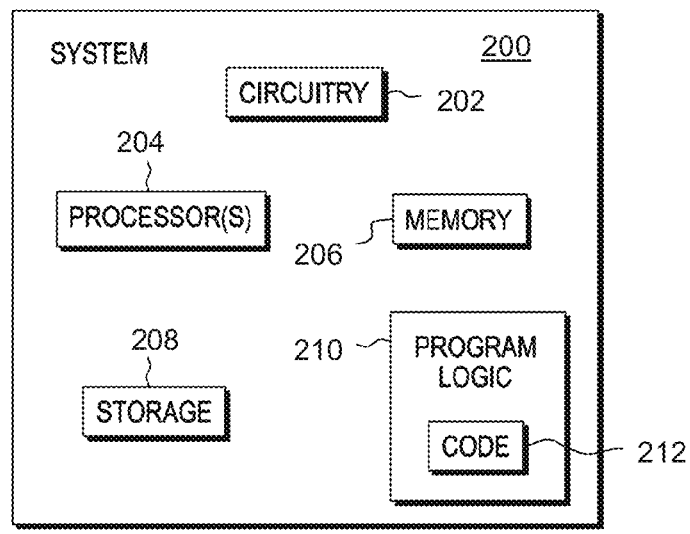
FIG. 2 depicts one embodiment of a single processor computing environment to incorporate and use one or more aspects of the present invention.

FIG. 2 illustrates a block diagram of a resource 200 in computer system 100, such as base computer 12 and auxiliary computers 18a-18c, which is part of the technical architecture of certain embodiments of the technique. Returning to FIG. 2, the resource 200 may include a circuitry 202 that may in certain embodiments include a microprocessor 204. The computer system 200 may also include a memory 206 (e.g., a volatile memory device), and storage 208. The storage 208 may include a non-volatile memory device (e.g., EEPROM, ROM, PROM, RAM, DRAM, SRAM, flash, firmware, programmable logic, etc.), magnetic disk drive, optical disk drive, tape drive, etc. The storage 208 may comprise an internal storage device, an attached storage device and/or a network accessible storage device. The system 200 may include a program logic 210 including code 212 that may be loaded into the memory 206 and executed by the microprocessor 204 or circuitry 202.

In certain embodiments, the program logic 210 including code 212 may be stored in the storage 208, or memory 206. In certain other embodiments, the program logic 210 may be implemented in the circuitry 202. Therefore, while FIG. 2 shows the program logic 210 separately from the other elements, the program logic 210 may be implemented in the memory 206 and/or the circuitry 202.

Figure 3:
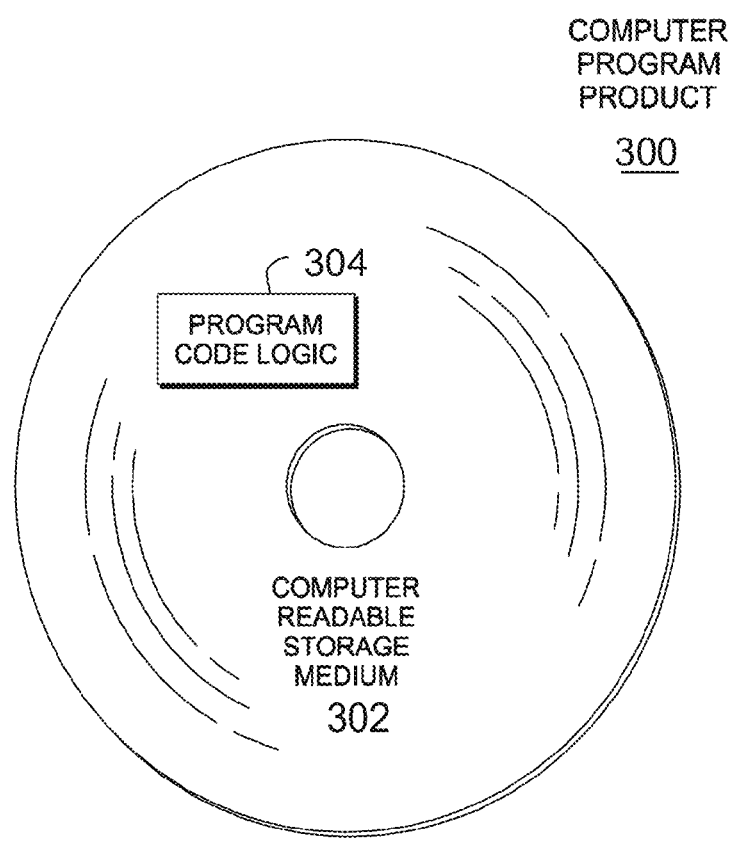
FIG. 3 depicts one embodiment of a computer program product incorporating one or more aspects of the present invention.

Using the processing resources of a resource 200 to execute software, computer-readable code or instructions, does not limit where this code can be stored. Referring to FIG. 3, in one example, a computer program product 300 includes, for instance, one or more non-transitory computer readable storage media 302 to store computer readable program code means or logic 304 thereon to provide and facilitate one or more aspects of the technique.

Figure 4:
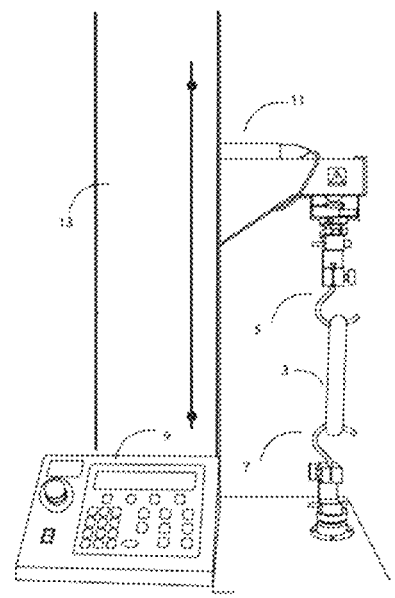
FIG. 4 depicts an aspect of one embodiment of a system incorporating one or more aspects of the present invention.

Referring to FIG. 4, in an embodiment of the present invention, a tensile test device can be communicatively coupled to a resource 200, such as that in FIGS. 1-2, for verifying mechanical properties of materials that can be processed utilizing software 10 executed by at least one processor in a computer system, such as resource 200, to determine the efficacy of an existing tourniquet and/or determine characteristics, such as ranges of pressure, that enable the effective design of additional exsanguination tourniquets. Aspects of this embodiment and methods for verifying the efficacy of an exsanguination tourniquet in accordance with the present technique will be discussed in greater detail later.

Figure 5A:
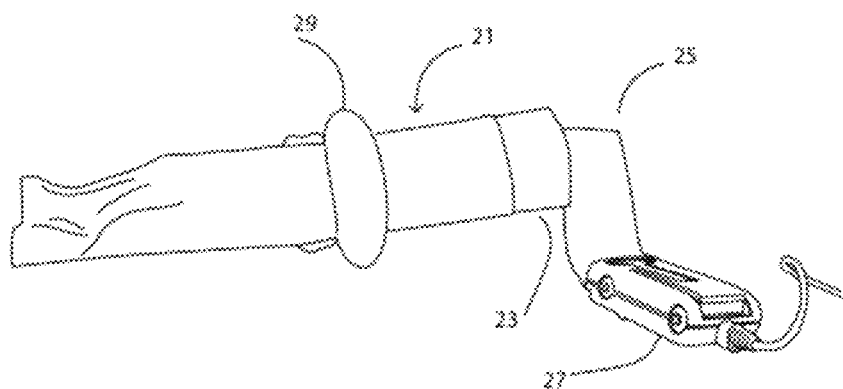
FIGS. 5A-5B depict an aspect of one embodiment of a system incorporating one or more aspects of the present invention.
Figure 5B:
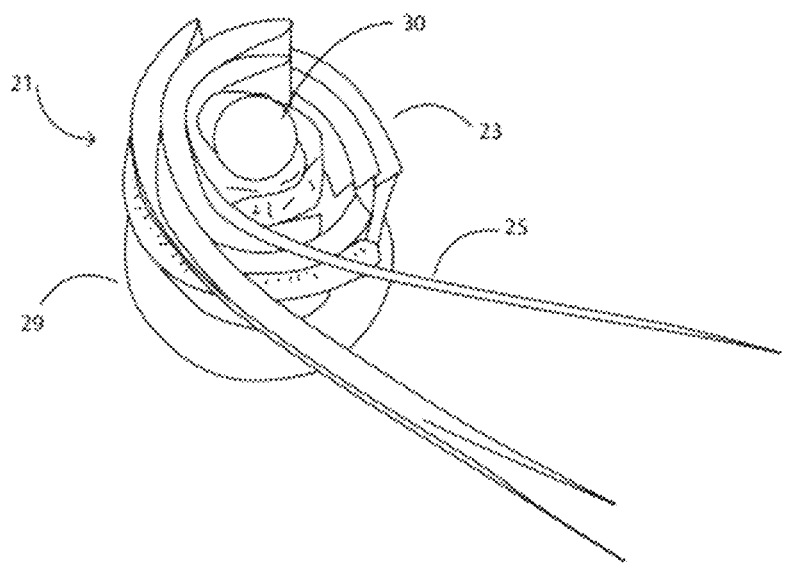

Referring to FIGS. 5A-5B, in an embodiment of the present invention, one or more tools 500 for verifying the pressure generated by a tourniquet can be communicatively coupled to a resource 200, such as that in FIGS. 1-2, for verifying the pressure generated by the tourniquet, which can be processed utilizing software 10 executed by at least one processor in a computer system, such as resource 200, to determine the efficacy of the tourniquet. FIG. 5A is a schematic view of a pressure measurement device for verifying the pressure generated by a tourniquet when applied to a limb model, while FIG. 5B is a schematic cross sectional view of a pressure measurement device for verifying the pressure generated by a tourniquet when applied to a limb model. Aspects of this embodiment and methods for verifying the efficacy of an exsanguination tourniquet in accordance with the present technique will be discussed in greater detail later.

As will be appreciated by one skilled in the art, aspects of the technique may be embodied as a system, method or computer program product. Accordingly, aspects of the technique may take the form of an entirely hardware embodiment, an entirely software embodiment (including firmware, resident software, micro-code, etc.) or an embodiment combining software and hardware aspects that may all generally be referred to herein as a "circuit," "module" or "system". Furthermore, aspects of the technique may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable signal medium may include a propagated data signal with computer readable program code embodied therein, for example, in baseband or as part of a carrier wave. Such a propagated signal may take any of a variety of forms, including, but not limited to, electro-magnetic, optical or any suitable combination thereof. A computer readable signal medium may be any computer readable medium that is not a computer readable storage medium and that can communicate, propagate, or transport a program for use by or in connection with an instruction execution system, apparatus or device.

A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Program code embodied on a computer readable medium may be transmitted using an appropriate medium, including but not limited to wireless, wireline, optical fiber cable, RF, etc., or any suitable combination of the foregoing.

Computer program code for carrying out operations for aspects of the technique may be written in any combination of one or more programming languages, including an object oriented programming language, such as Java, Smalltalk, C++ or the like, and conventional procedural programming languages, such as the "C" programming language, PHP, ASP, assembler or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the technique are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions, also referred to as software, such as the software 10 in FIG. 1, may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the technique. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In addition to the above, one or more aspects of the technique may be provided, offered, deployed, managed, serviced, etc. by a service provider who offers management of customer environments. For instance, the service provider can create, maintain, support, etc. computer code and/or a computer infrastructure that performs one or more aspects of the technique for one or more customers. In return, the service provider may receive payment from the customer under a subscription and/or fee agreement, as examples. Additionally or alternatively, the service provider may receive payment from the sale of advertising content to one or more third parties.

In one aspect of the technique, an application may be deployed for performing one or more aspects of the technique. As one example, the deploying of an application comprises providing computer infrastructure operable to perform one or more aspects of the technique.

As a further aspect of the technique, a computing infrastructure may be deployed comprising integrating computer readable code into a computing system, in which the code in combination with the computing system is capable of performing one or more aspects of the technique.

As yet a further aspect of the technique, a process for integrating computing infrastructure comprising integrating computer readable code into a computer system may be provided. The computer system comprises a computer readable medium, in which the computer medium comprises one or more aspects of the technique. The code in combination with the computer system is capable of performing one or more aspects of the technique.

Further, other types of computing environments can benefit from one or more aspects of the technique. As an example, an environment may include an emulator (e.g., software or other emulation mechanisms), in which a particular architecture (including, for instance, instruction execution, architected functions, such as address translation, and architected registers) or a subset thereof is emulated (e.g., on a native computer system having a processor and memory). In such an environment, one or more emulation functions of the emulator can implement one or more aspects of the technique, even though a computer executing the emulator may have a different architecture than the capabilities being emulated. As one example, in emulation mode, the specific instruction or operation being emulated is decoded, and an appropriate emulation function is built to implement the individual instruction or operation.

In an emulation environment, a host computer includes, for instance, a memory to store instructions and data; an instruction fetch unit to fetch instructions from memory and to optionally, provide local buffering for the fetched instruction; an instruction decode unit to receive the fetched instructions and to determine the type of instructions that have been fetched; and an instruction execution unit to execute the instructions. Execution may include loading data into a register from memory; storing data back to memory from a register; or performing some type of arithmetic or logical operation, as determined by the decode unit. In one example, each unit is implemented in software. For instance, the operations being performed by the units are implemented as one or more subroutines within emulator software.

Further, a data processing system suitable for storing and/or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

Figure 6:
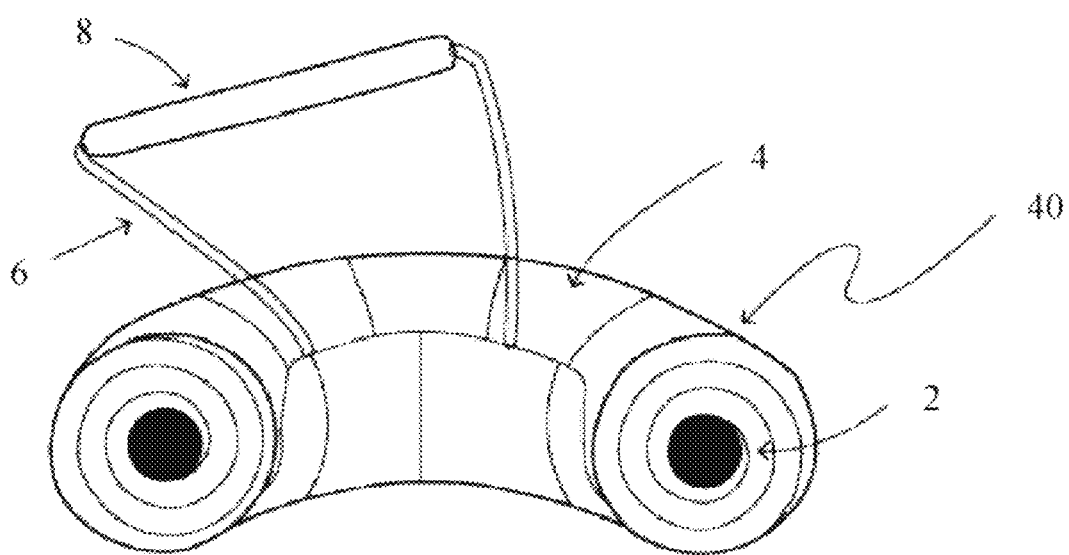
FIG. 6 depicts a cross-section of an exemplary exsanguination tourniquet.

FIG. 6 shows a cross section of an exsanguination tourniquet 40. The exsanguination tourniquet 40 issued as U.S. Pat. No. 7,854,748 which is herein incorporated by reference in its entirety. The other half of the exsanguination tourniquet 40 may be generally symmetrical to the portion shown in FIG. 6. The exsanguination tourniquet 40 may be constructed from an elastomeric ring 2 and may include an elastic sleeve 4 coupled to a plurality of straps 6 and wrapped around the elastomeric ring 2. The straps 6 may include at least one handle 8. As seen in FIG. 6, in general, an exsanguination tourniquet consists of at least one elastic ring which is wrapped around by an elastic sleeve.

Exsanguination tourniquets can be constructed in varying configurations and from a variety of materials. In general, an exsanguination tourniquet includes an elastic ring, which an elastic sleeve is wrapped around, as seen in FIG. 6, and described in greater detail above. However, some embodiments of the exsanguination tourniquets of the present invention include a constricting ring comprised of a flexible material, including but not limited to, steel. A constricting device in the exsanguination tourniquet can also include one or more concentric metallic springs, as described in greater detail below. In one example, a plurality of metallic springs are placed one inside the other to create the constricting portion of the exsanguination tourniquet. Given that limbs to which the exsanguination tourniquets are applied are not always uniform in circumference, some embodiments of the exsanguination tourniquets include an elastic ring and a non-uniform elastic sleeve, for example, a non-uniform sleeve with a conical shape. However, regardless of the materials that comprise the exsanguination tourniquet, aspects of the present technique enable optimization of the pressure level in order to achieve a uniform pressure profile over the length of the application site.

Figure 7:
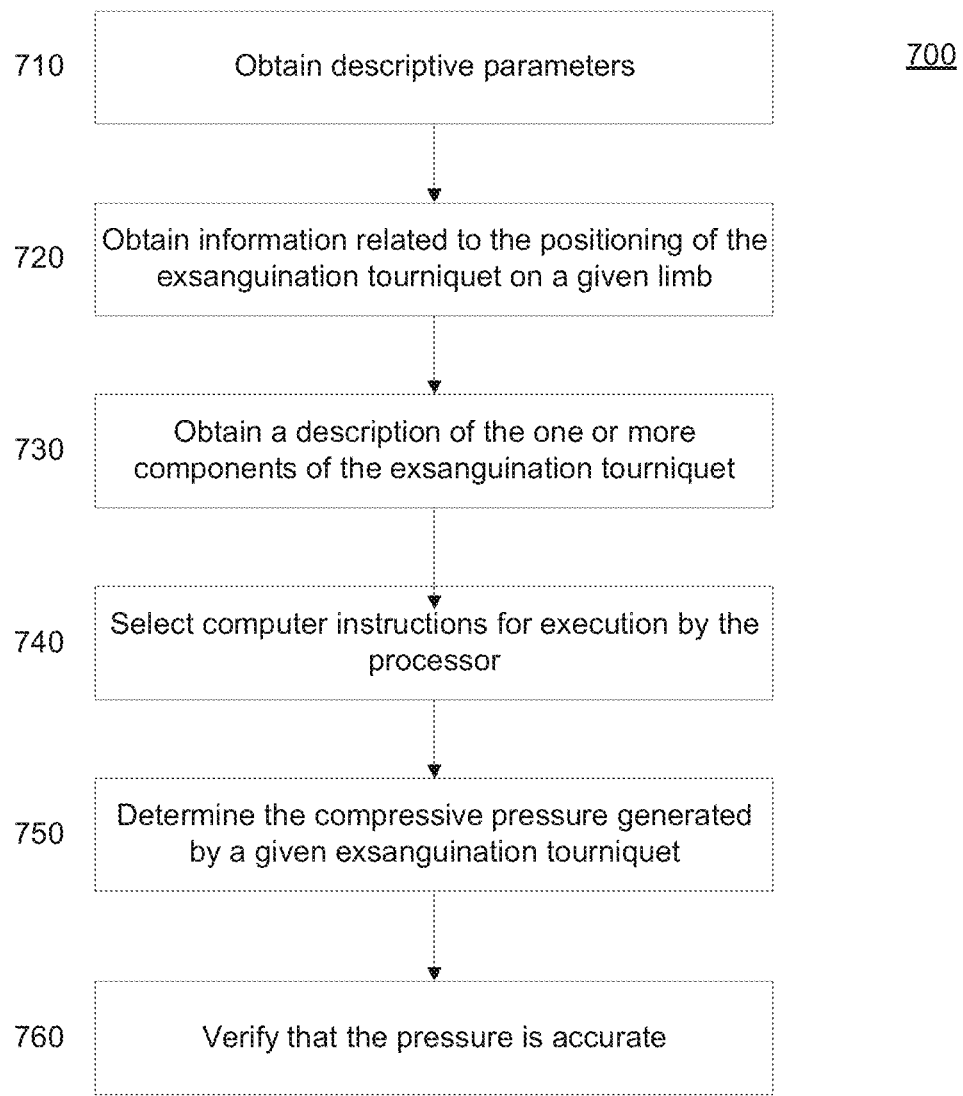
FIG. 7 depicts a workflow incorporating one or more aspects of an embodiment of the present invention.

FIG. 7 is an exemplary workflow 700 of the present invention that can be performed by a computer system, such as that in FIG. 1, utilizing resources, such as that in FIG. 2. For ease of understanding, the process of FIG. 7 is framed in the context of the system of FIG. 1, with reference to FIGS. 4 and 5.

Embodiments of the present invention can be utilized both to develop parameters that can be utilized in an exsanguination tourniquet to achieve the requisite pressure to operate efficiently and can also evaluate an existing exsanguination tourniquet to determine whether the desired pressure can be achieved given the properties of the exsanguination tourniquet and the application thereof. The workflow 700 of FIG. 7 utilizes aspects of an embodiment of the present invention to determine the pressure applied by a given exsanguination tourniquet in order to evaluate the efficacy of this exsanguination tourniquet.

An embodiment of the present technique can be used to determine whether an exsanguination tourniquet is being applied to a given site in an effective manner, but in order to make this determination, an embodiment of the technique first determines the pressure that is applied by a given exsanguination tourniquet at the given site. As aforementioned, embodiments of the present technique determine whether the pressure applied over the entire site to which the exsanguination tourniquet is applied is within an effective (predetermined) range as well as whether that pressure profile is uniform across the application site, e.g., a limb.

Referring to FIG. 7, the software 10 executed on one or more processors of a computer system obtains descriptive parameters 710 including, but not limited to, characteristics of the exsanguination tourniquet, including but not limited to, parameters related to the materials that comprise the given exsanguination tourniquet and physical dimensions of the exsanguination tourniquet. In embodiments of the present invention, parameters utilized by the software 10 vary in accordance with the composition of the exsanguination tourniquet.

When obtaining parameters related to a given exsanguination tourniquet, some embodiments of the present invention do not utilize values related to all components of the exsanguination tourniquet. For example, the software 10 can make a determination regarding whether the pressure in a given exsanguination tourniquet is consistent with maintaining a uniform pressure profile throughout and within an effective range by evaluating parameters related to one or more components of the exsanguination tourniquet, and/or all the combined components. Embodiments of the present invention can be utilized to determine the efficacy of a given exsanguination tourniquet based upon components, including but not limited to, an elastic ring, a spiral spring, a plurality of concentric spiral metallic springs, a combination of an elastic ring and elastic cylinder, and an elastic ring and at least one non-uniform elastic sleeve.

Alternatively, certain embodiments of the present technique can utilize parameters related to all elements of an exsanguination tourniquet to determine its efficacy. One embodiment of the present invention obtains parameters related to a plurality of tension generating circular elements and a plurality of sleeves of different parameters.

Parameters related to the exsanguination tourniquet obtained by the software 10 in various embodiments of the present technique vary depending upon the design and/or components of the exsanguination tourniquet. For example, for a tourniquet comprised of an elastic ring, parameters include, but are not limited to, the internal diameter of the ring before stretching it, the thickness of the ring before stretching it, the elastic constant of the ring from Hooke's law, and/or the thickness of the ring in the stretched mode at a desired distance from the tips of the toes or the fingers. For a constricting ring including a spiral spring made of steel or similar flexible material that is a component of an exsanguination tourniquet, parameters obtained by the software 10 include, but are not limited to, the wire diameter of the spring, the mean diameter of the spring before stretching it, the number of active coils in the spring, and/or the mean diameter of the spring in the stretched mode at a desired distance from the tips of the toes or the fingers. When obtaining the parameters of an exsanguination tourniquet that includes concentric spiral metallic springs, parameters include, but are not limited to, the wire diameter of the spring, the mean diameter of spring before stretching it, the number of active coils in spring, and/or the mean diameter of spring in the stretched mode when applied at a given distance from the tips of the toes or the fingers of a wearer. For an exsanguination tourniquet comprising an elastic ring and elastic cylinder, in an embodiment when parameters are obtained by the software 10 relating to both components, parameters obtained related to the elastic cylinder include, but are not limited to, the length of the elastic cylinder, the width of the elastic cylinder before stretching it, the thickness of the cylinder wall, the radial elastic constant of the elastic cylinder (from Hooke's law), and/or the contribution of the elastic cylinder to the thickness of the device in the stretched mode at a given distance from the tips of the toes or the fingers.

In addition to obtaining parameter information related to the exsanguination tourniquet, the software 10 also obtains information related to the positioning of the exsanguination tourniquet on a given limb 720. In embodiments of the present invention, the software 10 obtains the distance of the position of the exsanguination tourniquet on the limb relative to the tips of the toes or the fingers, depending upon the limb upon which the exsanguination tourniquet is placed and/or the limb circumference at this position.

In embodiments of the present invention, the software 10 executed on one or more processors of a computer resource obtains the descriptive parameters related to the exsanguination tourniquet and/or the placement data by communicating with external tools that are coupled to a computer resource that is accessible to a processor executing the software 10, over a communications network. These tools include, but are not limited to a tensile verification tool, such as that in FIG. 4.

FIG. 4 is a tensile test machine 400, which is a tool that is used, in embodiments of the present invention, for obtaining parameters related to tensile characteristics of the materials that comprise exsanguination tourniquets and the components of the exsanguination tourniquet, for example, an elastic ring, elastic spring, elastic sleeve, and/or the assembled tourniquet. The tool is utilized in embodiments of the present invention to verify the mechanical properties of these components. The tensile test machine 400 is an example of a device known in the art that can be utilized to obtain and/or verify the mechanical properties of elements comprising exsanguination tourniquets, as well as the assembled tourniquet. One of skill in the art will recognize that other known methods of evaluating these properties can be implemented and communicatively coupled to a computer resource accessible to software 10 executed by a processor to practice aspects of the disclosed technique.

In embodiments of the present invention, the tensile test machine 400 is used for testing a specimen 3 while being held on the upper hook 5 and the lower hook 7. The mobile base 11 of the upper hook 5 enables stretching of the specimen. The control panel 9 of the tensile test machine 400 is communicatively coupled to a computer resource accessible to the software 10. To obtain parameters related to the materials and components of the exsanguination tourniquet, the processor executes software 10 that instructs the tensile test machine to apply a known force to a component of an exsanguination tourniquet, and/or to set a specific elongation for a component of the exsanguination tourniquet. While the specimen is stretched by the tensile test machine 400, enabled by the software 10, the calibrated unit 13 measures both force and elongation. Since the pressure generated by any element/component is determined by its mechanical properties, the tensile test machine enables the software 10 to determine several parameters from the tensile test, including but not limited to K, the elastic constant of the component.

In further embodiments of the present invention, one or more of these parameters are entered via a user interface into a computer resource of the computer system practicing aspects of the technique.

In another embodiment of the present invention, one or more of the parameters utilized by the present invention are obtained by the software 10 from a memory device, such as a database, communicatively accessible to the one or more processors executing the software 10.

Returning to FIG. 7, in addition to obtaining descriptive parameters 710 and information related to the positioning of the exsanguination tourniquet on a given limb 720, the software 10 also obtains a description of the one or more components of the exsanguination tourniquet 730 to be used in determining the compressive pressure of the exsanguination tourniquet. As aforementioned, embodiments of the present invention can determine the compressive pressure of a given exsanguination tourniquet based on one or more of the components that comprise the exsanguination tourniquet. The software 10 obtains this information from a resource accessible to the computer resource executing the software 10, including but not limited to, inputs by a user through an input device on a computer resource accessible to the software 10 via a network connection, including but not limited to inputs into a specialized tool, such as those in FIGS. 4-5, and/or a standard input device known to one of skill in the art. In embodiments of the present invention, this information includes whether the exsanguination tourniquet includes one or more of the following components: an elastic ring, a spiral spring, a spiral metallic spring, an elastic cylinder, a non-uniform elastic sleeve, a circular element. In the embodiment of FIG. 7, the description obtained 730 can include both the identification of one or more components and the number of each of the identified components. For example, a given exsanguination tourniquet may contain more than one circular element and/or more than one elastic sleeve.

Once the software 10 obtains a description of the one or more components of the exsanguination tourniquet 730, the software 10 selects computer instructions (computer code) wherein the computer instructions comprise instructions for determining the compressive pressure of the exsanguination tourniquet 740. For ease of understanding, these instructions are represented throughout this specification as mathematical formulas (equations). These equations represent the relationship of the compressive pressure of an exsanguination tourniquet relative to various parameters obtained by the software 10. In embodiments of the present invention, the computer program selected by the software and subsequently executed by a processing resource in the computer system practicing the technique can be embodied in a stored procedure, a code fragment, a plain text file, etc., or any similar medium known to one of skill in the art and accessible by executing software 10, in various embodiments of the present invention.

The software 10 utilizes the selected program and the obtained parameters to determine the compressive pressure generated by a given exsanguination tourniquet 750. In general most cases, an exsanguination tourniquet consists of an elastic ring which is wrapped around by an elastic cylinder. For any specific limb of a circumference $C_{Limb}(x)$ at a position that is a distance $X_{Limb}$ from the tips of the toes or the fingers with a desired minimum compressive pressure $P_{Min}$ and a maximum compressive pressure $P_{Max}$, the software 10 utilizes a method represented by Equation 1 to calculate of the pressure generated by an elastic ring, when an elastic ring is identified as a component.

$$P(x) = \frac{\pi d_{Ring}(x) K_{Ring}\left(\frac{C(x)}{\pi} + d_{Ring}(x) - D_{Ring} - d_{Ring}\right)}{d_{Ring}^2\left(\frac{C(x)}{\pi} + d_{Ring}(x)\right)} \quad \text{Equation 1}$$

In Equation 1:

x=a position on the limb that is located at a distance $X_{Limb}$ from the tips of the toes or the fingers.

C(x)=the limb circumference at position x.

$D_{Ring}$=the internal diameter of the ring before stretching it.

$d_{Ring}$=the thickness of the ring before stretching it.

$K_{Ring}$=the elastic constant of the ring from Hooke's law.

$d_{Ring}(x)$=the thickness of the ring in the stretched mode at a distance $X_{Limb}$ from the tips of the toes or the fingers, calculated using the Poisson's ratio of the ring.

This elastic ring, when stretched, generates circumferential force and radial pressure that can be determined by the software 10.

In an embodiment of the present invention, the software 10 selects and utilizes a method represented by Equation 2 when determining the pressure generated by a constricting ring consisting of a spiral spring made of steel or similar flexible material.

$$P(x) = \frac{1000 \pi d_{sp}^4 (D_{sp}(x) + d_{sp})\left(\frac{C(x)}{\pi} + D_{sp}(x) - \frac{n_{sp} d_{sp}}{\pi} - D_{sp}\right)}{D_{sp}^3 n_{sp} (D_{sp} + d_{sp})^2 \left(\frac{C(x)}{\pi} + D_{sp}(x) + d_{sp}\right)} \quad \text{Equation 2}$$

In Equation 2:

x=a position on the limb that is located at a distance $X_{Limb}$ from the tips of the toes or the fingers.

$d_{sp}$=the wire diameter of the spring.

$D_{sp}$=the mean diameter of the spring before stretching it.

$n_{sp}$=the number of active coils in the spring.

$D_{sp}(x)$=the mean diameter of the spring in the stretched mode at a distance $X_{Limb}$ from the tips of the toes or the fingers, corrected for effect of elongation on $D_{sp}$.

In an embodiment of the present invention, the software 10 selects and utilizes a method represented by Equation 3 when determining the compressive pressure of an exsanguination tourniquet comprising concentric spiral metallic springs. This component includes a plurality of concentric spiral metallic springs that are placed one inside the other.

$$P(x) = \frac{\sum_{i=1}^{M} \frac{1000 \pi d_{sp_i}^4 (D_{sp_i}(x) + d_{sp_i})^2 \left(\frac{C(x)}{\pi} + D_{sp_i}(x) - \frac{n_{sp_i} d_{sp_i}}{\pi} - D_{sp_i}\right)}{D_{sp_i}^3 n_{sp_i}(D_{sp_i} + d_{sp_i})^2}}{\left(\frac{C(x)}{\pi} + D_{sp_M}(x) + d_{sp_M}\right)(D_{sp_M}(x) + d_{sp_M})} \quad \text{Equation 3}$$

In Equation 3:

x=a position on the limb that is located at a distance $X_{Limb}$ from the tips of the toes or the fingers.

$d_{spi}$=the wire diameter of spring i.

$D_{spi}$=the mean diameter of spring i before stretching it.

$n_{spi}$=the number of active coils in spring i.

$D_{spi}(x)$=the mean diameter of spring i in the stretched mode at a distance $X_{Limb}$ from the tips of the toes or the fingers, corrected for effect of elongation on $D_{spi}$.

In Equation 3, above, i goes from 1 to M, and M designates the properties of the external-most-spring.

An exsanguination tourniquet can comprise an elastic ring and an elastic cylinder, for example, an elastic constricting ring wrapped around by an elastic cylindrical sleeve comprises such an exsanguination tourniquet. In this case, in an embodiment of the present invention, the software 10 selects and applied a method represented by Equation 4 to calculate the compressive pressure.

$$P(x) = \quad \text{Equation 4}$$

$$\pi d_{Ring}^2(x) K_{Ring} \left(\frac{\frac{C(x)}{\pi} + d_{Ring}(x) + N(x) - D_{Ring} - d_{Ring}}{d_{Ring}^2}\right) + \frac{(K_{Cyl}(L_{Cyl} - x))(C(x) + \pi N(x) + \pi d_{Ring}(x) - 2W_{Cyl})}{\frac{C(x)}{\pi}(d_{Ring}(x) + N(x))}$$

The parameters for the ring are described in relation to Equation 1, but in Equation 4 for the elastic cylinder are as follows:

x=a position on the limb that is located at a distance $X_{Limb}$ from the tips of the toes or the fingers.

$L_{Cyl}$=the length of the elastic cylinder.

$W_{Cyl}$=the width of the elastic cylinder before stretching it.

$K_{Cyl}$=the thickness of the cylinder wall.

$K_{Cyl}$=the radial elastic constant of the elastic cylinder from Hooke's law.

N(x)=the contribution of the elastic cylinder to the thickness of the device in the stretched mode at a distance $X_{Limb}$ from the tips of the toes or the fingers.

Figure 8:
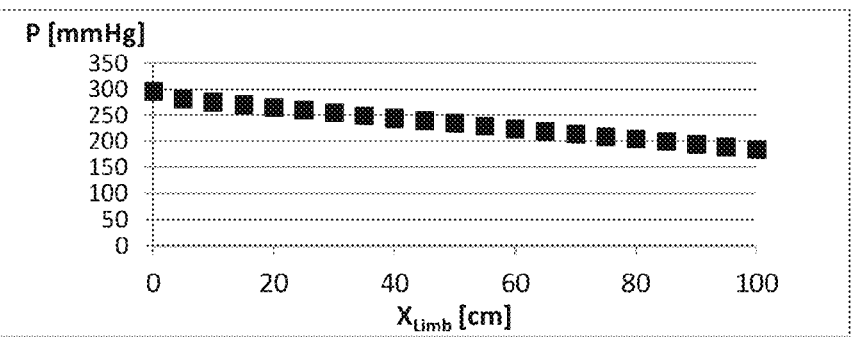
FIG. 8 depicts a graph illustrating a pressure generated by an elastic ring wrapped around by an elastic cylindrical sleeve, when applied to a uniform diameter cylinder, in accordance with one or more aspects of the present invention.
Figure 9:
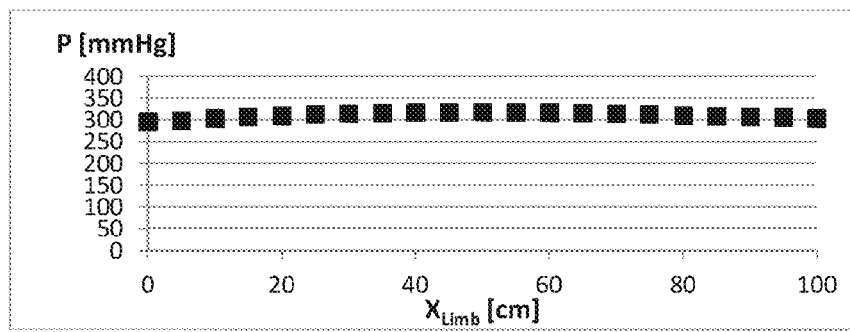
FIG. 9 depicts a graph illustrating the pressure when the elastic ring wrapped around by the elastic sleeve is applied over a conical shaped member, in accordance with one or more aspects of the present invention.

FIG. 8 is a graph showing the pressure generated by an elastic ring wrapped around by an elastic cylindrical sleeve, when applied to a uniform diameter cylinder. FIG. 9 shows the pressure when the elastic ring wrapped around by the elastic sleeve is applied over a conical shaped member from its narrower end (X=0) to its wider end (X=100 [cm]).

By selecting and applying a method embodied by a formula, the software 10 determines the compressive pressure. Returning to FIG. 7, once the software determines the compressive pressure, the software 10 evaluates whether the compressive pressure is optimized, i.e., whether the pressure is relatively uniform over the entire length of the conical limb as shown in FIG. 9.

In an embodiment of the present technique, designs produced by the technique are based on one or more of the following constraints: 1) the linear stretching range of the elastic elements (ring, sleeve and spring); 2) the thickness of the device shall be at least 15 [mm] (or 25[mm] in case of a grossly thick limb) at all times; 3) the ring dimensions (thickness and internal diameter) shall enable its rolling on the limb; 4) both the Young's modulus of the elastic elements and the thickness of the sleeve are limited due to production constraints; 5) the pressure profile exerted by the device shall be within the range of 150-350 [mm Hg] and shall be uniform—all values shall be within the range of ±20% that of the average pressure of the profile; 6) the elastic constant (K) of the spring is limited up to 0.05 [kg/mm] due to the mechanical properties of steel; 7) the maximal values of the following parameters are limited due to cost considerations: $D_{Ring}$, $L_{Cyl}$, $W_{Cyl}$, $d_{sp}$, $D_{sp}$ and $n_{sp}$.

Figure 10:
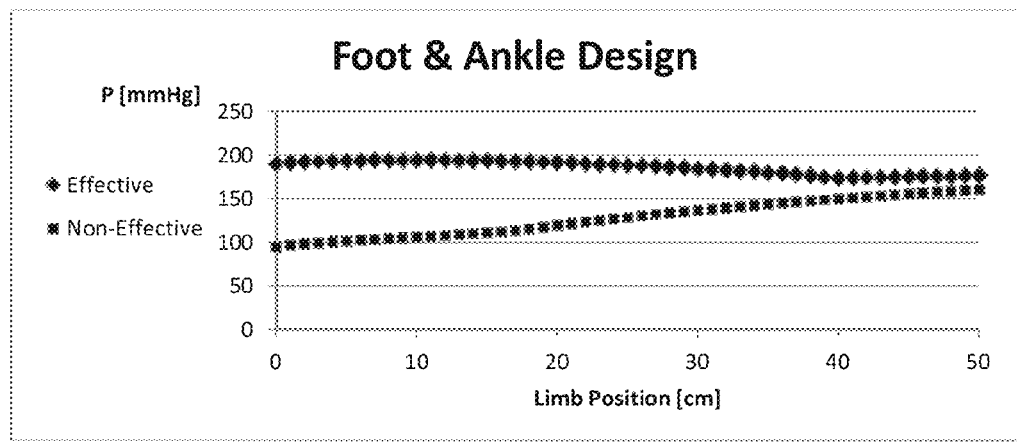
FIG. 10 depicts a graph illustrating the pressure profile exerted by two designs of a foot and ankle device, in accordance with one or more aspects of the present invention.

In an aspect of this embodiment, the constraints ensure that the design will be effective. For example, the pressure profile, in an exemplary exsanguination tourniquet wherein at least one parameter was determined by the present technique, is within the range of 150-350 [mmHg]. A pressure lower than 150 [mmHg] is less effective because it may not occlude the arterial blood flow, and a pressure greater than 350 [mmHg] is less effective because it may cause tissue injuries. FIG. 10 is a graph showing the pressure profile exerted by two designs of a foot and ankle device.

Referring to FIG. 10, the higher line on the graph is an effective design produced by the present technique as, with a pressure profile within the range of 150-350 [mmHg]. The lower line in FIG. 10 represents an ineffective design, as the sleeve of the tourniquet associated with this parameter is too wide. FIG. 10 demonstrates that the pressure of the non-effective design is below 150 [mmHg] along most of the limb and that utilizing this parameter in an exsanguination tourniquet may cause the tourniquet to fail.

An exsanguination tourniquet may also comprise an elastic ring and a non-uniform elastic sleeve. An embodiment of an invention applies the method in Equation 5 to determine the pressure applied by an elastic ring wrapped around by an elastic sleeve that has a non-uniform conical shape.

$$P(x) = \pi d_{Ring}^2(x) K_{Ring} \left( \frac{\frac{C(x)}{\pi} + d_{Ring}(x) + N(x) - D_{Ring} - d_{Ring}}{d_{Ring}^2} \right) + \frac{(K_{Cyl}(L_{Cyl} - x))(C(x) + \pi N(x) + \pi d_{Ring}(x) - 2W_{Cyl}(x))}{\frac{C(x)}{\pi}(d_{Ring}(x) + N(x))} \quad \text{Equation 5}$$

The majority of the parameters of Equation 5 are defined in Equation 4, for the elastic sleeve of Equation 5: $W_{Cyl}(x)$ =the width of the elastic sleeve before stretching it at a distance $X_{Limb}$ from the distal end of the limb.

As discussed earlier, a standard exsanguination tourniquet is comprised of one to a plurality of tension generating circular elements and one to a plurality of sleeves, in which the sleeves are optionally of different parameters. Upon receiving descriptive information indicating this configuration via an input, including but not limited to, a selection through a user interface, or a reading from a tool configured to communicated with a computer resource of a system practicing aspects of the method, the software 10 utilizes the method of Equation 6 below to determine the compressive pressure of the exsanguination tourniquet.

$$P(x) = \frac{\sum_{j=1}^{M} \left[ \frac{\pi d_j(x)^2 K_j}{d_j^2} \left( \frac{C(x)}{\pi} + \sum_{i=1}^{N} N_i(x) + d_j(x) - D_j - d_j \right) \right] + \sum_{i=1}^{N} \left[ K_i(L_i - x) \left( C(x) + \pi \sum_{i=1}^{N} N_i(x) + \pi d_M(x) - 2W_i(X) \right) \right]}{\frac{C(x)}{\pi} \left[ \sum_{i=1}^{N} N_i(x) + d_M(x) \right]} \quad \text{Equation 6}$$

In Equation 6, "M" defines the number of circular elements and "N" defined the number of circular sleeves.

For M circular elements:

x=a position on the limb that is located at a distance $X_{Limb}$ from the tips of the toes or the fingers.

=the internal diameter of the circular element j before stretching it.

$d_j$=the thickness of the circular element j before stretching it.

$K_j$=the elastic constant of the circular element j from Hooke's law.

$d_j(x)$=the thickness of the circular element j in the stretched mode at a distance $X_{Limb}$ from the distal end of the limb, calculated using the Poisson's ratio of the circular element.

For N elastic sleeves:

x=a position on the limb that is located at a distance $X_{Limb}$ from the tips of the toes or the fingers.

L=the length of sleeve i.

$W_i(x)$=the width of sleeve i before stretching it at a distance $X_{Limb}$ from the distal end of the limb.

$H_i(x)$=the thickness of sleeve i wall at a distance $X_{Limb}$ from the distal end of the limb.

$K_i$=the radial elastic constant of sleeve i from Hooke's law.

$N_i(x)$=the contribution of sleeve i to the thickness of the device in the stretched mode at a distance $X_{Limb}$ from the distal end of the limb.

In addition to providing parameters related to the mechanical properties of the elements, as well as the assembled tourniquet, herein disclosed are validation methods and devices for verifying and validating that a design of any exsanguination tourniquet, developed based on the unified equations and range of parameters disclosed in Table 1 below, meets the required specifications. These devices and methods can be divided into 2 groups:

1. Tools and methods for verifying the mechanical properties of the elements, as well as the assembled tourniquet.

2. Tools and methods for validating the pressure generated by an exsanguination tourniquet when applied to a limb-shaped simulator.

FIG. 7 described aspects of an embodiment of the technique when utilized to determine whether the compressive pressure of a given exsanguination tourniquet is optimal. However, embodiments of the present invention can also be utilized to assist in designing exsanguination tourniquets in accordance with the anatomical properties of an application site and the known optimal compressive pressure. Additionally, one of skill in the art will understand that the method can be utilized to locate an optimal application site given parameters describing the materials utilized in a given exsanguination tourniquet and the desired compressive pressure. To this end, an embodiment of the present technique was utilized to generate Table 1, shown below, which exhibits a range of values for each of the parameters for a number of specific anatomical dimensions of limbs. It is understood that one of skill in the art could utilize the present technique to determine other parameter value combinations for the examples below, as well as other limb dimensions.

TABLE 1

| | Ring | | | Sleeve | | | | Spring | | |
|---|---|---|---|---|---|---|---|---|---|---|
| | $D_{Ring}$ [mm] | $d_{Ring}$ [mm] | $E_{Ring}$ [MPa] | $L_{Cyl}$ [m] | $W_{Cyl}$ [cm] | $H_{Cyl}$ [mm] | $E_{Cyl}$ [MPa] | $d_{sp}$ [mm] | $D_{sp}$ [mm] | $n_{sp}$ |
| Thin leg | 29.9-77 | 0-30 | 0.16-1 | 0-3 | 8.4-20 | 0.4-4 | 0.05-0.4 | 0-3.5 | 0-60 | 0-240 |
| Normal leg | 40.8-77 | 0-30 | 0.16-1 | 0-3 | 9-20 | 0.4-4 | 0.05-0.4 | 0-3.5 | 0-60 | 0-240 |
| Thick leg | 49.2-77 | 0-30 | 0.16-1 | 0.1-3 | 14.2-20 | 0.4-4 | 0.05-0.4 | 0-3.5 | 0-60 | 0-240 |
| Grossly thick leg | 71.5-100 | 0-30 | 0.16-1 | 0.25-3 | 20-40 | 1.2-4 | 0.05-0.13 | 0-3.5 | 0-60 | 0-240 |
| Infant leg | 23.7-77 | 0-30 | 0.16-1 | 0.2-3 | 4-20 | 0.4-4 | 0.05-0.25 | 0-3.5 | 0-60 | 0-120 |
| Adult Arm | 21.9-77 | 0-30 | 0.16-1 | 0-3 | 5-20 | 0.4-4 | 0.05-0.39 | 0-3.5 | 0-60 | 0-120 |
| Foot and Ankle | 26-77 | 0-30 | 0.16-1 | 0-3 | 6.67-20 | 0.4-4 | 0.05-0.4 | 0-3.5 | 0-60 | 0-120 |
| Forearm | 24-77 | 0-30 | 0.16-1 | 0.1-3 | 4-20 | 0.4-4 | 0.05-0.4 | 0-3.5 | 0-60 | 0-120 |

Referring to Table 1, for the elastic ring, the following parameters are provided:

$D_{Ring}$=the internal diameter of the ring before stretching it.

$d_{Ring}$=the thickness of the ring before stretching it.

$E_{Ring}$=the Young's modulus of the ring.

Referring to Table 1, for the elastic sleeve:

$L_{Cyl}$=the length of the sleeve.

$W_{Cyl}$=the width of the sleeve before stretching it.

$H_{Cyl}$=the thickness of the sleeve wall.

$E_{Cyl}$=the Young's modulus of the sleeve.

Referring to Table 1, for the elastic spring:

$d_{sp}$=the wire diameter of the spring.

$D_{sp}$=the mean diameter of the spring before stretching it.

$n_{sp}$=the number of active coils in the spring.

Table 2 below represents the anatomical dimensions of the limbs referred to in Table 1.

TABLE 2

| | Initial Circumference [cm] | Final Circumference [cm] | Total Length [cm] |
|---|---|---|---|
| Thin leg | 25 ± 5 | 50 ± 10 | 100 ± 20 |
| Normal leg | 25 ± 5 | 70 ± 14 | 100 ± 20 |
| Thick leg | 25 ± 5 | 85 ± 17 | 100 ± 20 |
| Grossly thick leg | 25 ± 5 | 120 ± 24 | 100 ± 20 |
| Infant leg | 10 ± 2 | 35 ± 7 | 50 ± 10 |
| Adult Arm | 15 ± 3 | 35 ± 7 | 70 ± 14 |
| Foot and Ankle | 20 ± 4 | 40 ± 8 | 60 ± 12 |
| Forearm | 10 ± 2 | 35 ± 7 | 35 ± 7 |

Referring to Table 1, in an embodiment of the present technique, the range of values for the parameters in Table 1 is bounded based on one or more of the following constraints: 1) the linear stretching range of the elastic elements (ring, sleeve and spring); 2) the thickness of the device shall be at least 15 [mm] (or 25 [mm] in case of a grossly thick limb) at all times; 3) the ring dimensions (thickness and internal diameter) shall enable its rolling on the limb; 4) both the Young's modulus of the elastic elements and the thickness of the sleeve are limited due to production constraints; 5) the pressure profile exerted by the device shall be within the range of 150-350 [mm Hg] and shall be uniform—all values shall be within the range of ±20% that of the average pressure of the profile; 6) the elastic constant (K) of the spring is limited up to 0.05 [kg/mm] due to the mechanical properties of steel; 7) the maximal values of the following parameters are limited due to cost considerations: $D_{Ring}$, $L_{Cyl}$, $W_{Cyl}$, $d_{sp}$, $D_{sp}$ and $n_{sp}$.

Figure 11:
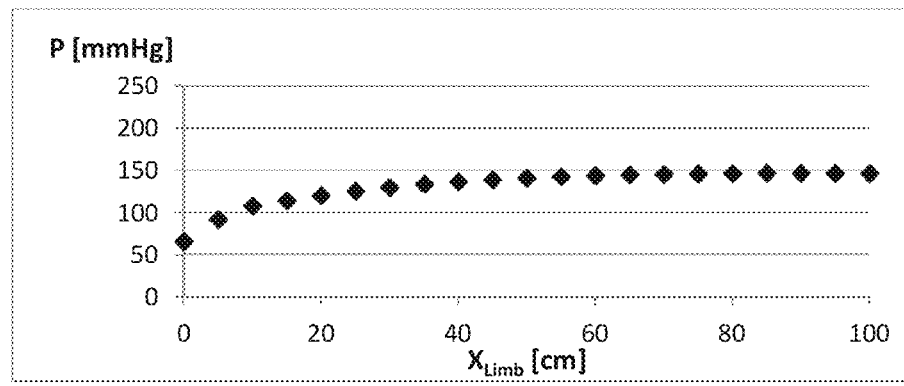
FIG. 11 depicts a pressure graph for a constricting elastic ring when stretched beyond its initial circumference ($C_O$) for a given set of parameter values, in accordance with one or more aspects of the present invention.

The effect of stretching the ring beyond initial circumference ($C_0$) for a given set of parameter values taken from Table 1 as applied to a limb geometry taken from Table 2 is shown in FIG. 11, where the X-axis is the distance starting from X=0 at the tips of the toes or the fingers in centimeters, and the Y-axis is the pressure in mm Hg at each location. As explained previously, the efficacy of an exsanguination tourniquet relies, in some part, upon the exsanguination tourniquet applying a nearly uniform compressive pressure across an application site, such as a limb.

Returning to FIG. 7, after the compressive pressure for a given exsanguination tourniquet application to a specific area is determined, the software 10 executed by a processor can verify that the pressure is accurate 760. In embodiments of the present invention, pressure measurements from an exsanguination tourniquet are obtained from a pressure measurement device 500 such as the device in FIGS. 5A-5B. Measurements from this tool can be utilized by the software 10 in systems to verify the pressure determined by the software 10 based on the parameters obtained and/or to verify the efficacy of an exsanguination tourniquet designed utilizing embodiments of the present invention.

Referring to FIGS. 5A-5B, a pressure measurement device 500 utilized in an embodiment of the present invention includes a limb model 21 (also called a limb simulator) that consists of several layers 23 for modeling different depths inside the limb. Each layer is covered along the simulated limb by an array of pressure sensors 25, which are sampled by a sensor measurement device 27 connected to a computer resource in an embodiment of the present invention. The pressure measurement device 500 is an example of a device known in the art that can be utilized to obtain and/or verify the pressure generated by an exsanguination tourniquet when applied to a limb-shaped simulator. One of skill in the art will recognize that other known methods of pressure on a limb simulator can be implemented and communicatively coupled to a computer resource accessible to software 10 executed by a processor to practice aspects of the disclosed technique.

While the tourniquet 29 is applied to the limb the generated pressure is measured according to the selected sensor (the selected depth). FIG. 5B, to which reference is now made, shows a cross-section of the limb model 21. The layers 23 of different depths are covered by the pressure sensors 25 which measure the pressure generated when the tourniquet 29 is applied to the simulated limb model. In the center of the limb model there is a rigid rod 30, which simulates a bone inside the limb. It is clear that by selecting different materials and dimensions it is possible to create different limb models, varying by shape, depths levels and stiffness.

Figure 12:
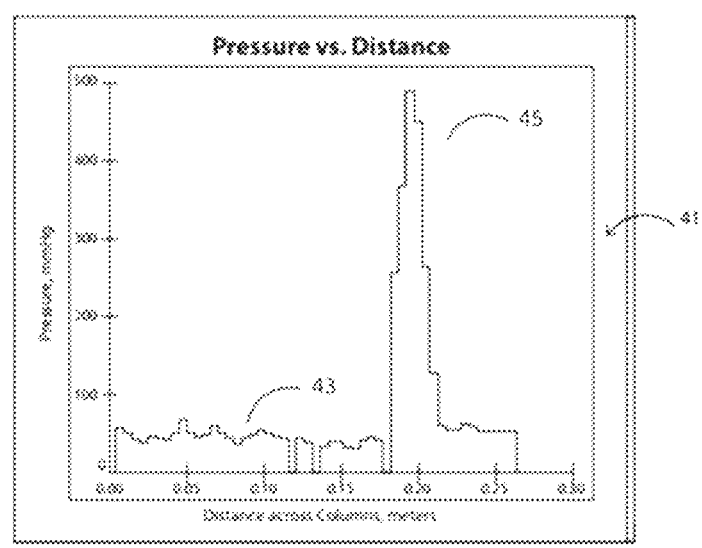
FIG. 12 depicts the pressure measurement results as shown in the software, in accordance with one or more aspects of the present invention.

An example of the pressure measurement results as shown in the software is shown in FIG. 12 to which reference is now made. The chart 41 shows the pressure distribution along the limb in the selected depth (according to the selected pressure sensor). The baseline pressure 43 is related to the limb's area which is unaffected by the tourniquet, while the peak pressure 45 is related to the limb's area affected by the constricting tourniquet. These results enable the validation of important parameters, such as: average pressure, peak pressure, total pressure and the area influenced by the tourniquet, which are critical for the validation of the unified equations described above.

Utilizing embodiments of the technique of the present invention, software 10 executed by a processor, can determine new designs and configurations for exsanguination tourniquets, based upon the compressive pressure and the parameters discussed related to the materials and characteristic of the materials that comprise the tourniquet as well as the characteristics of the site (limb) to which the newly determined configurations for exsanguination tourniquets will be applied. Embodiments of the present invention were utilized to produce exsanguination tourniquets that are optimized to accommodate the following sites: the foot and ankle, the forearm, an oversize thick leg, a grossly oversize thick leg. The following exsanguination tourniquets configurations determined utilizing aspects of embodiments of the present technique are offered as examples. One of skill in the art will recognize that the methods disclosed can be adapted to determine configurations for exsanguination tourniquets adapted to any and all application sites on a body, irrespective of the location of the site and any individual characteristics of the site.

An embodiment of the present technique was utilized to determine an original design for a ring and two sleeves exsanguination tourniquet for foot and ankle. An embodiment of the present technique was used to determine an original design for an exsanguination tourniquet comprising a ring and two sleeves for use on a forearm. An embodiment of the present invention was utilized to determine an exsanguination tourniquet configuration (design) for an oversize thick leg comprising a spring and two sleeves. An embodiment of the present invention was also utilized to determine a configuration for an exsanguination tourniquet for grossly oversize thick leg and the resultant exsanguination tourniquet comprises two springs and two sleeves.

The aforementioned exsanguination tourniquet including a ring and two sleeves adapted for the foot and ankle includes an elastic ring wrapped around by two elastic sleeves.

Figure 13:
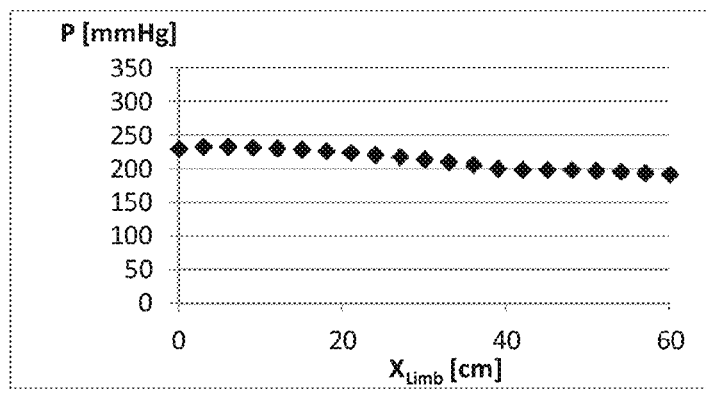
FIG. 13 depicts a graph illustrating the pressure generated by an embodiment of an exsanguination tourniquet, when applied to a conical shaped limb from its narrower end to its wider end, in accordance with one or more aspects of the present invention.

Table 3 below contains the parameters for this exsanguination tourniquet, derived utilizing an embodiment of the present invention. FIG. 13 is a graph depicting the pressure generated by this exsanguination tourniquet, when applied to a conical shaped limb from its narrower end to its wider end (from an initial circumference of 20 [cm] to a final circumference of 40 [cm] over a length of 60 [cm]).

TABLE 3

| | Parameter | Value | Tolerance |
|---|---|---|---|
| Ring | D [mm] | 40 | −2/+5 |
| | d [mm] | 25 | +1/−5 |
| | E [MPa] | 0.19 | ±0.03 |
| Elastic Sleeve | Length [m] | 0.4 | ±0.2 |
| | Width [cm] | 10 | ±1 |
| | Thickness [mm] | 1.1 | ±0.4 |
| | Young's Modulus [MPa] | 0.12 | ±0.05 |
| Additional Proximal Sleeve (Starts at: $X_{Limb}$ = 37 [cm]) | Length [m] | 0.3 | ±0.2 |
| | Width [cm] | 13 | ±3 |
| | Thickness [mm] | 1.1 | ±0.4 |
| | Young's Modulus [MPa] | 0.12 | ±0.05 |

Figure 14:
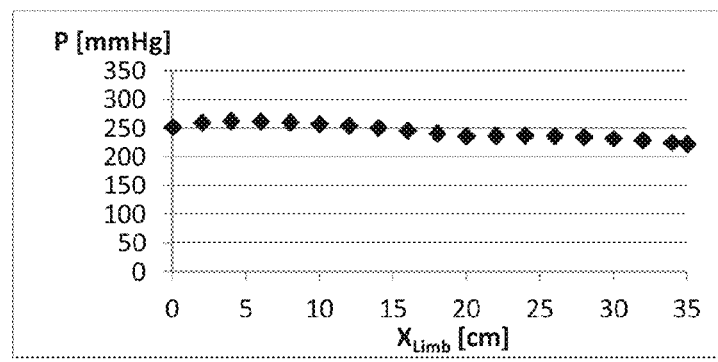
FIG. 14 depicts a graph illustrating the pressure generated by an embodiment of an exsanguination tourniquet, when applied to a conical shaped limb from its narrower end to its wider end, in accordance with one or more aspects of the present invention.

An embodiment of the present technique was utilized to determine an original design for a ring and two sleeved exsanguination tourniquet for a forearm. The resultant exsanguination tourniquet comprises an elastic ring wrapped around by two sleeves adapted for use on the forearm, the parameters of which are listed in Table 4. FIG. 14 is a graph depicting the pressure generated by such exsanguination tourniquet when applied to a conical shaped limb from its narrower end to its wider end (from an initial circumference of 10 [cm] to a final circumference of 35 [cm] over a length of 35 [cm]).

TABLE 4

| | Parameter | Value | Tolerance |
|---|---|---|---|
| Ring | D [mm] | 44 | ±8 |
| | d [mm] | 11 | ±3 |
| | E [MPa] | 0.25 | ±0.05 |
| Elastic Sleeve | Length [m] | 0.2 | ±0.05 |
| | Width [cm] | 5.5 | ±0.5 |
| | Thickness [mm] | 1 | ±0.3 |
| | Young's Modulus [MPa] | 0.12 | ±0.04 |
| Additional Proximal Sleeve (Starts at: $X_{Limb}$ = 20 [cm]) | Length [m] | 0.37 | ±0.03 |
| | Width [cm] | 8 | ±1 |
| | Thickness [mm] | 1 | ±0.1 |
| | Young's Modulus [MPa] | 0.12 | ±0.04 |

Figure 15:
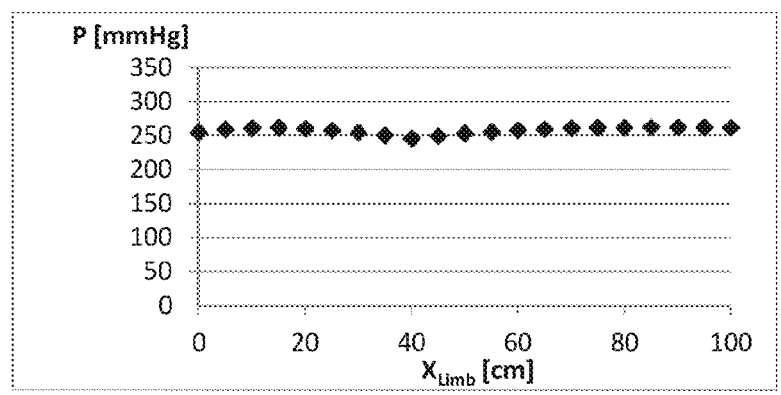
FIG. 15 depicts a graph illustrating the pressure generated by an embodiment of an exsanguination tourniquet, when applied to a conical shaped limb from its narrower end to its wider end, in accordance with one or more aspects of the present invention.

An embodiment of the present technique was utilized to determine an original design for an exsanguination tourniquet for an oversize thick leg. Table 2 defines the dimensions of an oversize thick leg. The resultant exsanguination tourniquet comprises a spring and two sleeves. The elastic ring in this device consists of a spiral spring made of steel and wrapped around by two sleeves. The parameters of this device are shown in Table 5. FIG. 15 shows the pressure generated by such exsanguination tourniquet when applied to a conical shaped limb from its narrower end to its wider end (from an initial circumference of 25 [cm] to a final circumference of 85 [cm] over a length of 100 [cm]).

TABLE 5

| | Parameter | Value | Tolerance |
|---|---|---|---|
| Spring | D [mm] | 24 | ±2 |
| | d [mm] | 2.4 | ±0.2 |
| | n | 75 | ±5 |
| Elastic Sleeve | Length [m] | 1.8 | ±0.4 |
| | Width [cm] | 18 | ±2 |
| | Thickness [mm] | 1 | ±0.4 |
| | Young's Modulus [MPa] | 0.12 | ±0.04 |
| Additional Distal Sleeve (Starts at: $X_{Limb} = 0$) | Length [m] | 0.4 | ±0.2 |
| | Width [cm] | 10 | ±2 |
| | Thickness [mm] | 1 | ±0.4 |
| | Young's Modulus [MPa] | 0.12 | ±0.04 |

Figure 16:
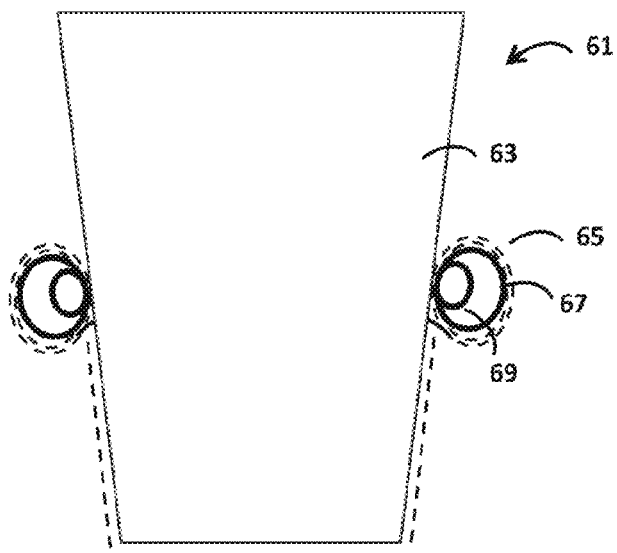
FIG. 16 is a schematic cross-sectional view of an embodiment of an exsanguination tourniquet, in accordance with one or more aspects of the present invention.

FIG. 16 shows a cross-section of an embodiment of an exsanguination tourniquet 61 including a plurality of coiled concentric spring members 67, 69 and at least one sleeve 65. The device is applied to a limb 63, for example, a conical shaped limb, and consists of an internal spring member 69 placed inside an external spring member 67 which is wrapped around by at least one sleeve 65. The at least one sleeve 65 may be, for example, two elastic cylindrical sleeves. The two elastic cylindrical sleeves 65 may partially overlap both while wrapped around the constricting member 67, 69 and when deployed onto the patient's limb 63. In addition, although not shown, it is also contemplated that the exsanguination tourniquet 61 may include at least one strap and at least one handle on the strap for deploying the exsanguination tourniquet 61 on the patient's limb 63. The at least one strap and at least one handle may be of the type shown in FIG. 6 and described in greater detail above, in U.S. Pat. No. 7,854,748 and International Application No. PCT/IL2013/050563, each of which is herein incorporated by reference in their entireties. Further, the exsanguination tourniquet 61 may be used with an applicator device, such as applicator device 170, as described in greater detail below.

Figure 17:
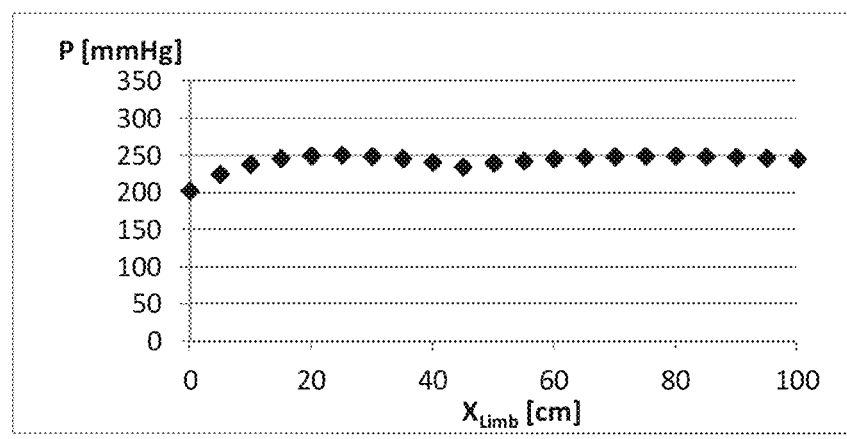
FIG. 17 depicts a graph illustrating the pressure generated by an embodiment of an exsanguination tourniquet, when applied to a conical shaped limb from its narrower end to its wider end, in accordance with one or more aspects of the present invention.

A configuration for an exsanguination tourniquet, as seen in FIG. 16 may be utilized for placement of a grossly oversize thick leg, as defined by the parameters to Table 2. An embodiment of the present invention is utilized to determine this design wherein the constricting member in this device consists of, for example, two spiral concentric spring members made of a flexible metal such as steel, placed one inside the other and wrapped around by two sleeves. Exemplary parameters determined by an embodiment of the present invention for this exsanguination tourniquet are listed in Table 6. FIG. 17 is a graph that depicts the pressure generated by this exsanguination tourniquet when applied to a conical shaped limb from its narrower end to its wider end (from an initial circumference of 25 [cm] to a final circumference of 120 [cm] over a length of 100 [cm]).

TABLE 6

| | Parameter | Value | Tolerance |
|---|---|---|---|
| External Spring | D [mm] | 42 | ±4 |
| | d [mm] | 3 | ±0.3 |
| | n | 80 | ±12 |
| Internal Spring | D [mm] | 33 | ±4 |
| | d [mm] | 3 | ±0.3 |
| | n | 80 | ±12 |
| Elastic Sleeve | Length [m] | 1.8 | ±0.4 |
| | Width [cm] | 24 | ±4 |
| | Thickness [mm] | 1.3 | ±0.3 |
| | Young's Modulus [MPa] | 0.16 | ±0.03 |
| Additional Distal Sleeve | Length [m] | 0.45 | ±0.05 |
| | Width [cm] | 11 | ±0.5 |

TABLE 6-continued

| | Parameter | Value | Tolerance |
|---|---|---|---|
| (Starts at: $X_{Limb} = 0$) | Thickness [mm] | 1.8 | ±0.2 |
| | Young's Modulus [MPa] | 0.1 | ±0.02 |

Figure 18:
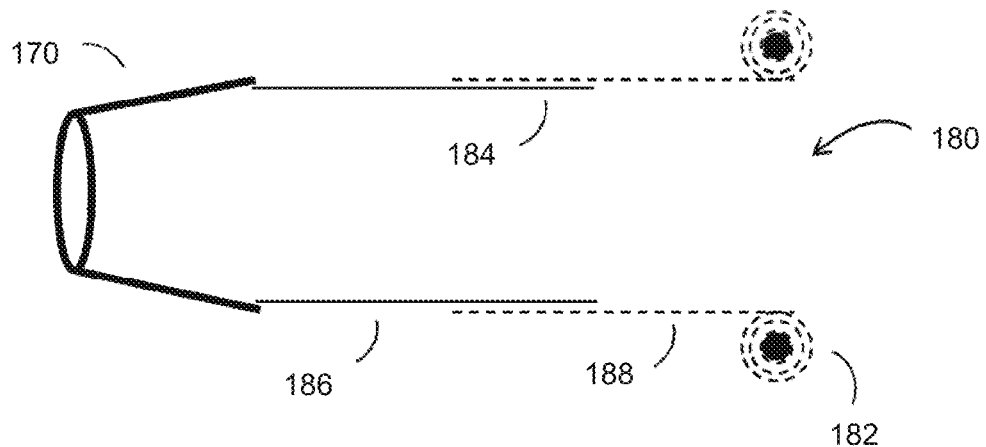
FIG. 18 depicts a side cross-sectional view of an exsanguination tourniquet system, in accordance with one or more aspects of the present invention.
Figure 19:
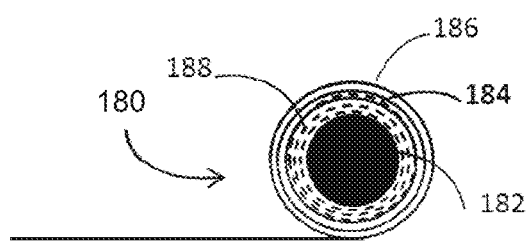
FIG. 19 depicts a cross-sectional view of an embodiment of the exsanguination tourniquet of FIG. 16, in accordance with one or more aspects of the present invention.

FIGS. 18-19 depict different views of an embodiment of an exsanguination tourniquet 180 utilizing the aforementioned two sleeve configuration and can be utilized on a foot, ankle, leg, and forearm, as described above. The exsanguination tourniquet 180 may include a constricting member 182 and at least one sleeve 186, 188. The exsanguination tourniquet 180 may also include an applicator device 170. The applicator device 170 may be of the type disclosed in International Application No. PCT/IL2013/050563, which is incorporated herein by reference in its entirety. In the depicted embodiment, the at least one sleeve 186, 188 may be wrapped around the constricting member 182, as shown in FIG. 18. Then the at least one sleeve 186, 188 may optionally be applied over the applicator device 170 as the exsanguination tourniquet 180 is deployed over the patient's limb, as shown in FIG. 18. Further, the exsanguination tourniquet 180 may include at least one strap (not shown) secured to the constricting member 182 to assist with placing the exsanguination tourniquet 180 onto the patient. The at least one strap (not shown) may also include at least one handle (not shown) to assist with placing the exsanguination tourniquet 180 onto the patient's limb. The at least one strap and at least one handle may be of the type shown in FIG. 6 and described in greater detail above and in U.S. Pat. No. 7,854,748 and PCT/IL2013/050563, each of which is incorporated herein by reference in their entireties.

The at least one sleeve 186, 188 may be, for example, a single sleeve (not shown) or multiple overlapping sleeves, such as, a first sleeve 186 and a second sleeve 188 which overlap in region 184. Additional numbers of sleeves are also contemplated as would be understood by one of ordinary skill in the art to cover larger or longer limbs. As depicted in FIGS. 18-19, the at least one sleeve includes a first sleeve 186 which may be, for example, a distal sleeve, and a second sleeve 188 which may be, for example, a proximal sleeve. The sleeves 186, 188 may be separate sleeves which overlap in the region 184, although it is also contemplated that the sleeves 186, 188 may be coupled or secured together in the region 184 to create a single sleeve. The sleeves 186, 188 may overlap by, for example, approximately 3-5 [cm], although other amounts of overlap are also contemplated depending on the parameters required for excluding blood from the patient's limb. An exsanguination tourniquet 180 with multiple independent sleeves 186, 188, which overlap during deployment onto a patient, enables easy removal of the first sleeve 186 after deployment is complete to expose the surgical site or field, while keeping the second sleeve 188 on the patient's limb.

The constricting member 182 may be, for example, a generally ring-shaped member that enables the at least one sleeve 186, 188 to couple to the constricting member 182 for deploying the exsanguination tourniquet 180 onto a patient's limb. The constricting member 182 may have, for example, a generally circular cross-section to enable easier rolling of the exsanguination tourniquet 180 onto the patient's limb. The constricting member 182 may be, for example, an elastic ring or at least one spring member. The elastic ring may be, for example, an elastic member, such as a silicon ring or ring made of another elastic material as known by one of ordinary skill in the art which can expand and contract. The at least one spring member may be, for example, at least one ring shaped spring member which may be a coiled spring that forms a ring.

Figure 21:
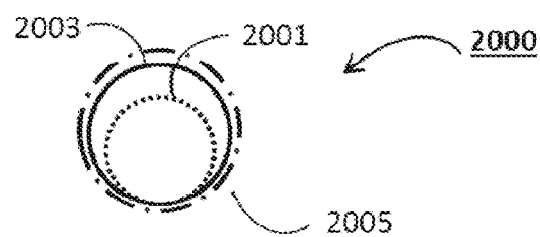
FIG. 21 depicts a cross-sectional view of the exsanguination tourniquet of FIG. 16, in accordance with one or more aspects of the present invention.

In embodiments which use multiple spring members, the spring members may each be, for example, coiled spring members that each form a ring and the spring members may be fit inside of each other. For example, as shown in FIG. 21, a first spring member 2001 may be positioned inside of a second spring member 2003. The first and second spring members 2001, 2003 may have, for example, a generally circular cross-section to enable easier rolling of the exsanguination tourniquet 2000 onto the patient's limb. The first spring member 2001 may be, for example, an internal spring member and it is contemplated that multiple internal spring members may be used to obtain the desired pressure on the patient's limb to exclude blood from the patient's limb while the exsanguination tourniquet 2000 is deployed. The exsanguination tourniquet 2000, of FIG. 21, may also include at least one sleeve 2005. The second spring member 2003 may be, for example, an external spring member and the at least one sleeve 2005 may be wrapped around the second spring member 2003.

Figure 20:
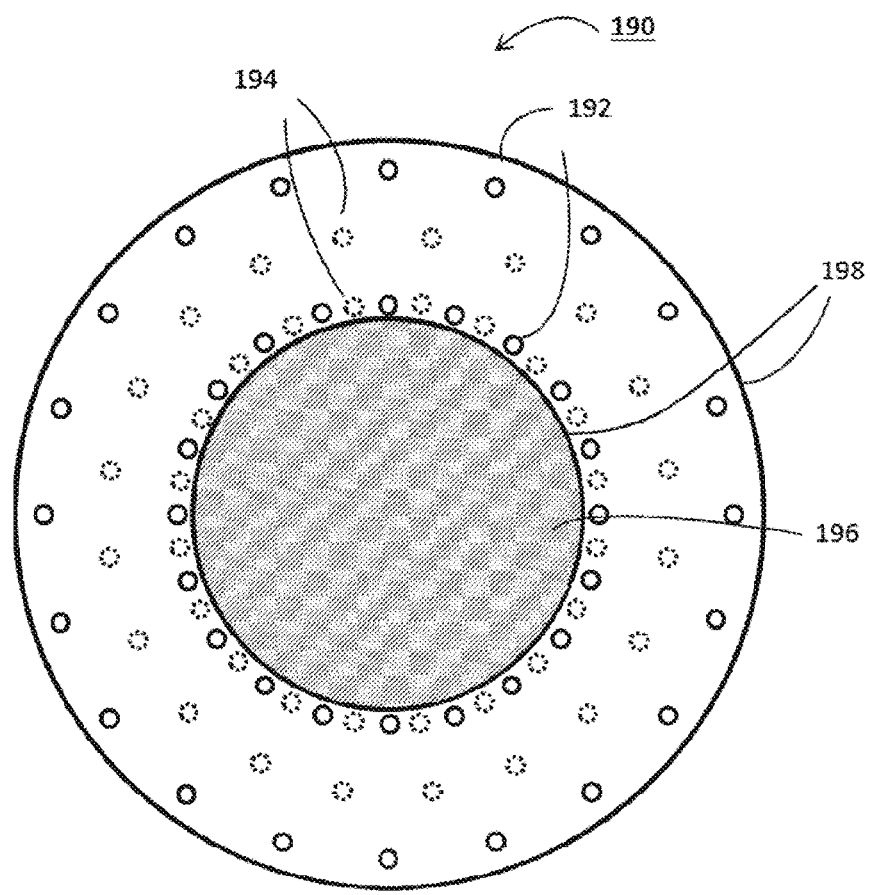
FIG. 20 depicts a cross-sectional view of the exsanguination tourniquet of FIG. 16, in accordance with one or more aspects of the present invention.

FIG. 20 depicts a two spring member embodiment of an exsanguination tourniquet 190. A cross-section of the exsanguination tourniquet 190 is shown after being deployed on the patient's limb 196. As shown in FIG. 20, a first spring member 194 may be positioned inside the second spring member 192. To enable the first spring member 194 to be positioned inside of the second spring member 192, the outer diameter of the first spring member 194 will be smaller than the inner diameter of the second spring member 192. The first spring member 194 may include a plurality of coils and each coil is represented by two dots in FIG. 20. Likewise, the second spring member 192 may include a plurality of coils and each coil is represented by two dots in FIG. 20. The first and second spring members 194, 192 may have, for example, a generally circular cross-section to enable easier rolling of the exsanguination tourniquet 190 onto the patient's limb. As the exsanguination tourniquet 190 is deployed on the patient's limb 196 both spring members 192, 194 may apply a force on the limb 196 to exclude blood out of the patient's limb 196. As the spring members 192, 194 are deployed onto the patient's limb 196, the spring members 192, 194 stretch radially and the distance between the coils increases. As depicted in FIG. 20, as the exsanguination tourniquet 190 is deployed onto the patient's limb 196 the distance between the coils of the external circumference of each spring member 192, 194 is larger than the distance between the coils of the internal circumference of each spring member 192, 194 which contact the patient's limb. In addition, as the exsanguination tourniquet 190 is rolled over the patient's limb 196, at least one sleeve, such as sleeve 198, is deployed onto the patient's limb 196 to maintain pressure on the limb 196 and restrict blood flow to the patient's limb 196. The sleeve 198 may be wrapped around the spring members 192, 194 prior to being rolled out onto the patient's limb 196. The spring members used in the exsanguination tourniquets 190, 2000 may include a plurality of coils and the number of coils is dependent upon the desired properties of the spring member, as described in greater detail above with reference to Table 1. In addition, the number of coils in each spring member will be dependent upon the dimensions of the patient's limb.

The exsanguination tourniquet embodiments of FIGS. 20-21 may also include at least one strap (not shown) secured to the external spring members 192, 2003 of the constricting members to assist with placing the exsanguination tourniquets 190, 2000 onto the patient. The at least one strap (not shown) may also include at least one handle (not shown) to assist with placing the exsanguination tourniquet 190, 2000 onto the patient's limb. The at least one strap and at least one handle may be of the type shown in FIG. 6 and described in greater detail above and in U.S. Pat. No. 7,854,748 and PCT/IL2013/050563, each of which is incorporated herein by reference in their entireties. In addition, the at least one sleeve 198, 2005 may optionally be applied over the applicator device 170, as described in greater detail above, as the exsanguination tourniquet 190, 2000 is deployed over the patient's limb.

The exsanguination tourniquets 61, 180, 190, 2000, as shown in FIGS. 16 and 18-21, may be used on a patient's limbs, for example, a patient's foot, ankle, leg, hand, wrist, and arm. The exsanguination tourniquets 61, 180, 190, 2000 may include a constricting member, for example, an elastic ring 182 or at least one spring member 67, 69, 192, 194 or 2001, 2003, and at least two sleeves 65, 186, 188, 198, 2005. The elastic ring 182 and the at least one spring member 67, 69, 192, 194 or 2001, 2003 may be formed to exert a desired tension force on to the patient's limb. The tension forces of the elastic ring 182 and/or the at least one spring member 67, 69, 192, 194 or 2001, 2003 are determined by the dimensions, materials, and mechanical properties of the elastic ring 182 and/or the at least one spring member 67, 69, 192, 194, 2001, 2003. Where there are at least two springs, such as in the embodiments of FIGS. 16, 20, and 21 each spring may have a different dimension so that they may fit inside of each other, may each be made of the same or different material, and may each have the same or different material properties. Based on the desired pressure profile, an elastic ring 182, at least one spring member 67, 69, 192, 194 or 2001, 2003, or any combination thereof may be selected with the dimensions, materials, and mechanical properties necessary to achieve the desired pressure profile, which may be determined as described in greater detail above with reference to FIGS. 1-17. Also as described in greater detail above, the exsanguination tourniquets 61, 180, 190, 2000 may be formed with the desired parameters based on the materials used and the number of constricting members and sleeves used to exclude a patient's blood from their limb without causing tissue damage. For example, the at least one spring member 67, 69, 192, 194, 2001, 2003 may be made of a metal, such as, stainless steel, and the elastic ring 182 may be made of silicone or another elastic material. At least one spring member 67, 69, 192, 194 or 2001, 2003 may be used instead of an elastic ring 182 for the constricting member to reduce costs and make it easier for the surgeon to roll the constricting member over the patient's limb in order to exclude the patient's blood. Although not shown, it is also contemplated that an elastic ring may be positioned inside at least one spring member to form yet another embodiment exsanguination tourniquet.

The exsanguination tourniquets 61, 180, 190, 2000 may be made based on the parameters discussed above with reference to FIGS. 8-17 and which will not be described again here for brevity sake. The parameters may be used to optimize the blood exclusion from a patient's limbs using the exsanguination tourniquets 180, 190, 2000. Exclusion may include both exsanguination or removing the blood from the patient's limb and arterial occlusion or preventing the re-entry of blood into the limb.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. An exsanguination tourniquet, comprising:
   a constricting member comprising a closed elastic ring; and
   at least two elastic cylindrical sleeves removably coupled to the constricting member, wherein the at least two elastic cylindrical sleeves are rolled onto the constricting member;
   wherein the at least two elastic cylindrical sleeves partially overlap along a longitudinal axis;
   wherein the constricting member and at least one of the at least two elastic cylindrical sleeves are configured to apply radial pressure to a limb within a range of 150 to 350 mm Hg to exsanguinate and occlude arterial blood flow into the limb; and
   wherein the constricting member and the at least two elastic cylindrical sleeves are configured to apply a substantially uniform radial pressure profile along the limb.

2. The exsanguination tourniquet of claim 1, wherein the constricting member further comprises:
   at least one spring member; and
   wherein the closed elastic ring is positioned inside of the at least one spring member.

3. The exsanguination tourniquet of claim 1, wherein the constricting member further comprises:
   at least one spring member.

4. The exsanguination tourniquet of claim 3, wherein the at least one spring member comprises:
   a first spring member; and
   a second spring member positioned inside of the first spring member.

5. The exsanguination tourniquet of claim 4, wherein the first spring member comprises a first coiled spring and the second spring member comprises a second coiled spring, wherein the first coiled spring has a larger diameter than the second coiled spring.

6. The exsanguination tourniquet of claim 5, wherein the first coiled spring and the second coiled spring comprise a plurality of coils.

7. The exsanguination tourniquet of claim 1, wherein the at least two elastic cylindrical sleeves comprise:
   a first elastic cylindrical sleeve; and
   a second elastic cylindrical sleeve partially overlapping the first elastic cylindrical sleeve.

8. The exsanguination tourniquet of claim 7, wherein the first elastic cylindrical sleeve has a first end and a second end and the second elastic cylindrical sleeve has a first end and a second end, wherein the second end of the first elastic cylindrical sleeve has a first diameter that is larger than a first diameter of the first end of the second elastic cylindrical sleeve, and wherein the first end of the first elastic cylindrical sleeve has a second diameter that is larger than a second diameter of the second end of the second elastic cylindrical sleeve.

9. The exsanguination tourniquet of claim 1, wherein the constricting member and the at least two elastic cylindrical sleeves are configured to apply the substantially uniform radial pressure profile along the limb with pressure values that are within 20% of the average radial pressure of the profile to exsanguinate and occlude arterial blood flow into the limb.

10. The exsanguination tourniquet of claim 1, wherein at least one of the at least two elastic cylindrical sleeves has a conical shape.

* * * * *